US00PP25257P3

(12) United States Plant Patent
Li

(10) Patent No.: US PP25,257 P3
(45) Date of Patent: Jan. 27, 2015

(54) *VERBENA* PLANT NAMED 'KLEVP13441'

(50) Latin Name: *Verbena* sp.
Varietal Denomination: KLEPVP13441

(71) Applicant: Klemm+Sohn GmbH & Co. KG, Stuttgart (DE)

(72) Inventor: Ruijun Li, North Parramatta (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 53 days.

(21) Appl. No.: 13/986,458

(22) Filed: May 6, 2013

(65) Prior Publication Data

US 2014/0331372 P1 Nov. 6, 2014

(51) Int. Cl.
*A01H 5/02* (2006.01)

(52) U.S. Cl.
USPC ..... Plt./308

(58) Field of Classification Search
CPC ..... A01H 5/02
USPC ..... Plt./308
See application file for complete search history.

*Primary Examiner* — June Hwu
*Assistant Examiner* — Keith Robinson
(74) *Attorney, Agent, or Firm* — Barbara Campbell; Cochran Freund & Young LLC

(57) ABSTRACT

A new *Verbena* plant particularly distinguished by burgundy flowers and a semi-upright growth habit, is disclosed.

1 Drawing Sheet

Genus and species: *Verbena* sp.
Variety denomination: 'KLEVP13441'.

BACKGROUND OF THE NEW PLANT

The present invention comprises a new and distinct variety of *Verbena*, botanically known as *Verbena* sp., and hereinafter referred to by the variety name 'KLEVP13441'. 'KLEVP13441' originated from a cross-pollination conducted in June 2008 in Sydney, Australia between the proprietary female *Verbena* variety '07.15.35' (unpatented), and the proprietary male *Verbena* variety '15.79.03' (unpatented).

The seeds from the cross were sown and plants were grown in a greenhouse for evaluation, where an individual plant designated 'KLEVP13441' was selected from the group of plants in October 2008.

In January 2009, 'KLEVP13441' was first vegetatively propagated by vegetative stem cuttings in Sydney, Australia. 'KLEVP13441' was found to reproduce true to type in successive generations of asexual propagation via vegetative stem cuttings in Stuttgart, Germany.

CROSS REFERENCE TO RELATED APPLICATIONS

Plant Breeder's Rights for 'KLEVP13441' were applied for in Canada on Feb. 8, 2013, Application No. 13-7929. 'KLEVP13441' has not been made publicly available or sold more than one year prior to the filing date of this application.

SUMMARY

The following are the most outstanding and distinguishing characteristics of this new variety when grown under normal horticultural practices in Stuttgart, Germany.

1. Burgundy flowers; and
2. A semi-upright growth habit.

DESCRIPTION OF THE PHOTOGRAPH

This new *Verbena* plant is illustrated by the accompanying photograph which shows the plant's overall plant habit including form, foliage, and flowers. The photograph is of a five-month-old plant grown outdoors in Stuttgart, Germany in April 2011. The colors shown are as true as can be reasonably obtained by conventional photographic procedures.

DESCRIPTION OF THE NEW VARIETY

The following detailed descriptions set forth the distinctive characteristics of 'KLEVP13441'. The data which define these characteristics were collected from asexual reproductions carried out in Stuttgart, Germany. Data was collected on three-month-old plants grown in a greenhouse in Stuttgart, Germany in February 2013. Color references are to The R.H.S. Colour Chart of The Royal Horticultural Society of London (R.H.S.), 5$^{th}$ edition (2007).

Classification:
- *Family*.—Verbenaceae.
- *Botanical*.—*Verbena* sp.
- *Common*.—*Verbena*.
- *Designation*.—'KLEVP13441'.

Parentage:
- *Female parent*.—The proprietary *Verbena* variety '07.15.35' (unpatented).
- *Male parent*.—The proprietary *Verbena* variety '15.79.03' (unpatented).

Plant:
- *Growth and branching habit*.—Semi-upright, well-branching.
- *Height (from top of soil)*.—25.0 cm.
- *Width (horizontal plant diameter)*.—40.0 cm.
- *Time to produce a finished flowering plant*.—About 10 weeks.
- *Time to initiate and develop roots*.—About 30 days.
- *Root description*.—RHS 158C (White), normal, smooth roots with an ovate shape.

Stems:
- *Number of branches per plant*.—Greater than 6.
- *Growth habit*.—Stems growing from the middle.

*Length*.—About 20.0 cm.
*Diameter*.—20.0 cm to 25.0 cm.
*Internode length*.—About 3.0 to 4.0 cm.
*Color*.—RHS 135C.
*Anthocyanin*.—Absent.
*Texture and appearance*.—Shiny, ovate, and slightly pubescent.

Leaves:
*Arrangement*.—Opposite.
*Immature and mature leaf*.—Color: Upper surface: RHS 135B. Lower surface: RHS 135C.
*Length*.—2.5 cm.
*Width*.—1.5 cm.
*Shape*.—Lanceolate.
*Apex*.—Cuspidate.
*Base*.—Truncate.
*Margin*.—Serrate.
*Texture* (*both upper and lower surfaces*).—Leathery.
*Venation type*.—Pinnate.
*Venation color* (*both upper and lower surfaces*).—Darker than RHS 135B.
*Petioles*.—Length: About 0.1 cm. Diameter: About 0.1 cm. Color: RHS 135B. Texture: Leathery.

Flower buds:
*Shape*.—Tall, cylindrical.
*Length*.—About 1.0 cm.
*Diameter*.—0.1 cm.
*Color* (*at tight bud*).—RHS 135C.

Inflorescence:
*Blooming habit* (*flowering season*).—Continuously.
*Lastingness of individual blooms on the plant*.—High, around one week.
*Fragrance*.—Absent.
*Inflorescence type*.—Umbel.
*Length of inflorescence*.—About 2.0 to 3.0 cm.
*Diameter of inflorescence*.—About 6.0 cm.
*Number of florets per inflorescence*.—About 20.
*Peduncle*.—Color: RHS 61A. Length: About 2.0 cm. Diameter: About 0.1 cm.

Florets:
*Length*.—About 2.0 cm.
*Diameter*.—About 2.0 cm.
*Color*.—RHS 61C.
*Appearance*.—Shiny.
*Form*.—Single.
*Length*.—About 2.0 cm.
*Diameter*.—About 2.0 cm.
*Color* (*both immature and mature*).—Upper surface: RHS 61C. Lower surface: RHS 61D.
*Corolla tube length*.—0.5 cm.
*Corolla tube color* (*both inner and outer surfaces*).—RHS 131B.
*Petals*.—Length of lobe: About 1.0 cm. Diameter of lobe: 0.5 cm. Lobe shape: Reniform. Apex: Obtuse. Base: Acute. Margin: Sinuate. Appearance (both upper and lower surfaces): Shiny. Arrangement: Free.
*Pedicels*.—Length: 1.0 cm. Diameter: 0.5 cm. Color: RHS 61D. Appearance: Shiny.

Sepals:
*Arrangement*.—Calyx is composed of more than 10 sepals arranged in a single row.
*Shape*.—Round.
*Apex*.—Obtuse, vase-shaped.
*Base*.—Obtuse, vase-shaped.
*Margin*.—Entire.
*Length*.—0.5 cm.
*Diameter*.—Greater than 0.1 cm.
*Color*.—RHS 143D.
*Appearance* (*both upper and lower surfaces*).—Leathery.

Reproductive organs:
*Stamens*.—Quantity: 5. Appearance: Shiny. Color: RHS 131D. Filament length: About 3.0 cm. Filament diameter: About 1.0 cm. Anther: Color: RHS 131C. Length: About 1.0 cm. Diameter: 0.1 cm. Pollen amount: None, sterile.
*Pistils*.—Number: 1. Length: 1.0 cm. Diameter: Less than 0.1 cm. Stigma: Color: RHS 143D. Appearance: Shiny. Length: 0.1 cm. Diameter: Less than 0.1 cm. Style: Color: RHS 143D. Length: Shiny. Diameter: 0.1 cm. Appearance: Shiny.

Fruit and seed set: No fruit and seed set observed.
Disease and pest/insect resistance: Resistant to mildew (*Podosphaera xanthii*).

COMPARISON WITH PARENTAL LINES AND KNOWN VARIETIES

'KLEVP13441' is distinguished from its parents as described in Table 1.

TABLE 1

Comparison with Parental Lines

| Characteristic | 'KLEVP13441' | Female Parent '07.15.35' | Male Parent '15.79.03' |
|---|---|---|---|
| Growth and branching | Strong growth, well-branching | Strong growth, not as branching as 'KLEVP13441' | Compact growth |

'KLEVP13441' is most similar to the commercial *Verbena* varieties 'Empress Purple' (unpatented) and 'Vepita Dark Magenta' (unpatented). Differences between the three varieties are described in Table 2.

TABLE 2

Comparison with Similar Varieties

| Characteristic | 'KLEVP13441' | 'Empress Purple' | 'Vepita Dark Magenta' |
|---|---|---|---|
| Growth habit | Semi-upright | Upright, trailing | |
| Flower color | Burgundy | Upper surface is RHS 72A (Red-Purple) and lower surface is RHS 72C (Red-Purple) | Lighter than 'KLEVP13441' |

I claim:

1. A new and distinct variety of *Verbena* plant designated 'KLEVP13441' as shown and described herein.

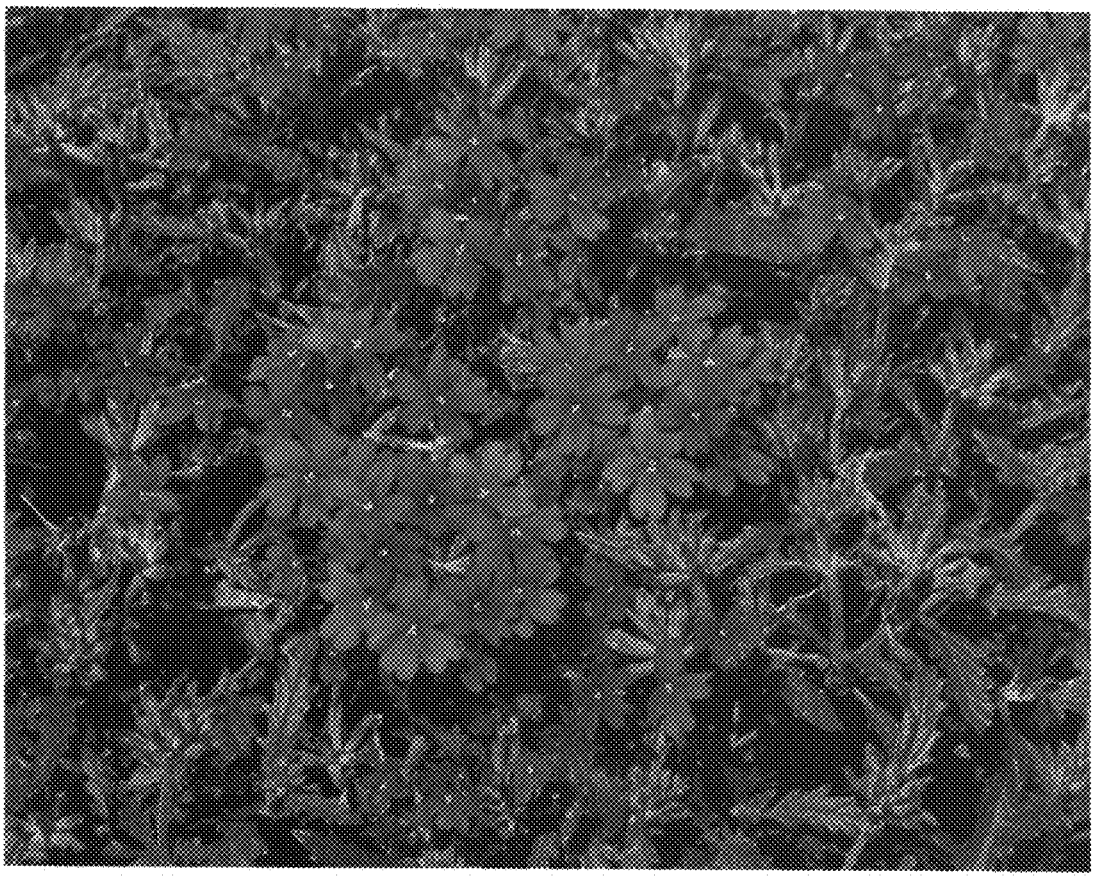

* * * * *